(12) United States Patent
Xu et al.

(10) Patent No.: US 9,227,900 B2
(45) Date of Patent: Jan. 5, 2016

(54) METHOD FOR PREPARING 1-(4-CHLOROPHENYL)-2-CYCLOPROPYL-1-PROPANONE AND INTERMEDIATE THEREOF

(71) Applicant: JIANGSU CHENGYANG CROP SCIENCE CO., LTD, Nanjing (CN)

(72) Inventors: Minghua Xu, Nanjing (CN);
Shangcheng Xu, Nanjing (CN);
Xiaojun Wang, Nanjing (CN);
Chuanhui Yu, Nanjing (CN); Qin Wan, Nanjing (CN); Jiabin Hu, Nanjing (CN)

(73) Assignee: Jiangsu Chengyang Crop Science Co., Ltd., Nanjing (CN)

( * ) Notice: Subject to any disclaimer, the term of this patent is extended or adjusted under 35 U.S.C. 154(b) by 0 days.

(21) Appl. No.: 14/442,739

(22) PCT Filed: Nov. 18, 2013

(86) PCT No.: PCT/CN2013/087296
§ 371 (c)(1),
(2) Date: May 14, 2015

(87) PCT Pub. No.: WO2014/079344
PCT Pub. Date: May 30, 2014

(65) Prior Publication Data
US 2015/0299078 A1    Oct. 22, 2015

(30) Foreign Application Priority Data

Nov. 22, 2012  (CN) .......................... 2012 1 0479107

(51) Int. Cl.
C07C 45/42        (2006.01)
C07C 41/30        (2006.01)

(52) U.S. Cl.
CPC ................. *C07C 45/42* (2013.01); *C07C 41/30* (2013.01)

(58) Field of Classification Search
USPC .......................... 568/306, 313, 329, 316, 317
See application file for complete search history.

(56) References Cited

U.S. PATENT DOCUMENTS 6,291,721 B1 * 9/2001 Hu .......................... C07C 41/01
568/426

* cited by examiner

*Primary Examiner* — Fereydoun G Sajjadi
*Assistant Examiner* — Pancham Bakshi
(74) *Attorney, Agent, or Firm* — Oliff PLC

(57) ABSTRACT

A method is for preparing 1-(4-chlorophenyl)-2-cyclopropyl-1-propanone and an intermediate thereof, where in the method for preparing a compound of formula (I), α-alkoxy p-chlorobenzyl phosphonate (II) and cyclopropyl methyl ketone are used as raw materials, and subjected to a Homer-Wadsworth-Emmons reaction in an organic solvent in the presence of a base, so as to prepare a derivative of alkoxy propylene with the structure of formula (III); and the resulting derivative of alkoxy propylene (III) is hydrolyzed under acidic conditions to obtain 1-(4-chlorophenyl)-2-cyclopropyl-1-propanone (I).

8 Claims, No Drawings

METHOD FOR PREPARING 1-(4-CHLOROPHENYL)-2-CYCLOPROPYL-1-PROPANONE AND INTERMEDIATE THEREOF

This application is the U.S. national phase of International Application No. PCT/CN2013/087296 filed on 18 Nov. 2013 which designated the U.S. and claims priority to Chinese Application Nos. 201210479107.X filed on 22 Nov. 2012, the entire contents of each of which are hereby incorporated by reference.

FIELD OF THE INVENTION

The present invention relates to the field of chemistry and chemical engineering, and to a process for preparing 1-(4-chlorophenyl)-2-cyclopropyl-1-propanone, an intermediate thereof, and a process for preparing the intermediate.

BACKGROUND OF THE INVENTION 1-(4-chlorophenyl)-2-cyclopropyl-1-propanone (I) is a key intermediate used in the production of the of fungicide cyproconazole.

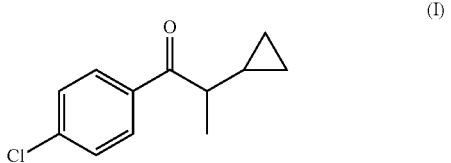

The several known methods for preparation of the above compound are described in the prior literature, such as, U.S. Pat. No. 4,664,696, CN101786948A, RU2350579, CN101125807A, U.S. Pat. No. 4,973,767, and CN101857576 A. However, said methods require using dangerous and/or highly toxic chemicals, and, in some cases, would be difficult for industrialization because of hardly controlled reaction process, high production cost and the like.

DESCRIPTION OF THE INVENTION

Accordingly, an objective of the present invention is to provide a new process for preparing 1-(4-chlorophenyl)-2-cyclopropyl-1-propanone (I) in order to avoid the disadvantages mentioned hereinabove.

Another objective of the present invention is to provide a derivative of alkoxy propylene represented by a structural formula (III).

A further objective of the present invention is to provide a process for preparing a derivative of alkoxy propylene represented by a structure formula (III).

The objectives of the present invention can be achieved by the following approaches:

There is provided a process for preparing a compound of formula (I), where α-alkoxy p-chlorobenzyl phosphonate with the structure of formula (II) and cyclopropyl methyl ketone are subjected to a Horner-Wadsworth-Emmons reaction in the presence of a base so as to prepare a derivative of alkoxy propylene with the structure of formula (III), and then the resulting derivative (III) is hydrolyzed to obtain the compound of formula (I), 1-(4-chlorophenyl)-2-cyclopropyl-1-propanone;

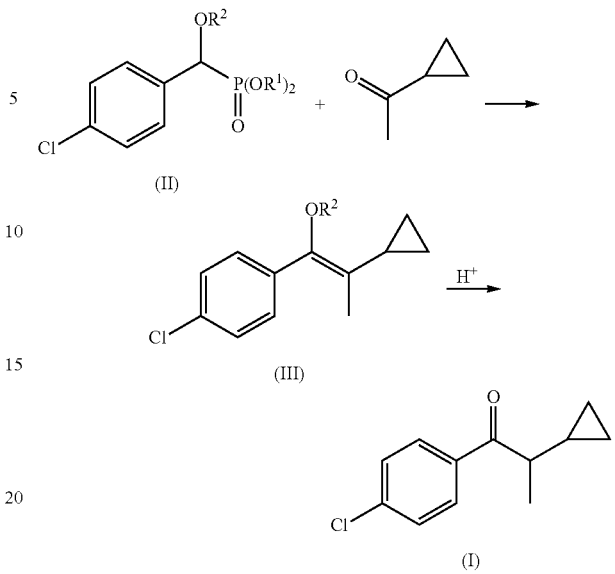

where, $R^1$ is methyl or ethyl; and $R^2$ is a C1-C4 alkyl, such as methyl, ethyl, n-propyl, isopropyl or n-butyl, preferably methyl or ethyl.

Bases suitable for use in the process of the invention refers to an inorganic alkali or organic alkali with a strong alkalinity, including sodium amide, sodium hydride, lithium diisopropylamide, and an alkali metal alkoxide such as sodium methoxide, sodium ethoxide, sodium isopropoxide, sodium isobutoxide, potassium isobutoxide, sodium tert-butoxide, or potassium tert-butoxide, and is preferably sodium amide, sodium tert-butoxide or potassium tert-butoxide.

Organic solvent used in the process of the invention is generally selected from one or more of polar solvents including methanol, ethanol, 1-propanol, isopropanol 1-butanol, isobutanol, tert-butanol, dimethyl formamide, dimethyl acetamide, N-methyl-pyrrolidone, dimethyl sulfoxide, dioxane or tetrahydrofuran, or a mixture of one or more of the aforementioned polar solvents and a non-polar solvent such as benzene, toluene, dichloromethane or dichloroethane.

In the process of the present invention, the molar ratio of α-alkoxy p-chlorobenzyl phosphonate (II), cyclopropyl methyl ketone and the base is 1.0-1.5:1.0-1.5:1.5-4.0, preferably 1.0-1.2:1.0-1.2:2.0-2.5; the reaction temperature is 0° C. to 40° C., preferably 10° C. to 30° C.; and the reaction time is 2 h to 8 h.

In the process of the invention, the derivative of alkoxy propylene (III) is hydrolyzed to prepare 1-(4-chlorophenyl)-2-cyclopropyl-1-propanone (I) under acidic conditions, wherein an acid used in the hydrolysis reaction may be hydrochloric acid, sulfuric acid, acetic acid, phosphoric acid or potassium dihydrogen phosphate, and is preferably hydrochloric acid; a reaction medium is water, or a mixture of water and an organic solvent such as methanol, ethanol, isopropanol tert-butanol, dichloromethane, dichloroethane, tetrahydrofuran, dimethyl formamide, dimethyl sulfoxide or toluene; the reaction temperature is 20° C. to 40° C.; and the reaction time is 3 h to 10 h.

In the process of the invention, α-alkoxy p-chlorobenzyl phosphonate (II) as a starting material is prepared according to the methods recorded in the literature, such as Justus Liebigs Annalen der Chemie, (1), 88-100 (1977); JOC, 56 (6), 2240-2244 (1991); Synthesis, (4), 330-332 (1984);

IN2003MU00079 (2005); Organic Letters, 11 (17), 3882-3885 (2009) and Tetrahedron Letters, 49 (46), 6501-6504 (2008). The synthetic route for preparation of the α-alkoxy p-chlorobenzyl phosphonate (II) is as follows.

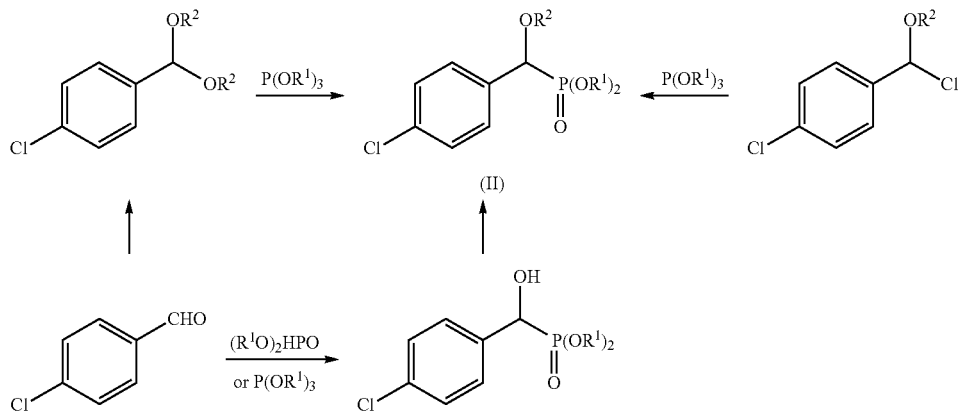

Where, definitions of R$^1$ and R$^2$ are the same as above.

The present invention further provides a derivative of alkoxy propylene represented by a structure of formula (III),

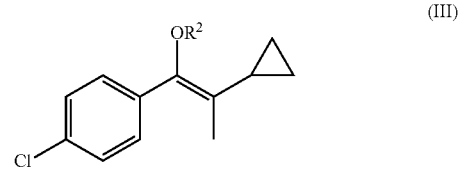

where, R$^2$ represents a C1-C4 alkyl, such as methyl, ethyl, n-propyl, isopropyl or n-butyl, preferably methyl or ethyl. The derivative of alkoxy propylene with the structure of formula (III) is an intermediate used in the preparation of 1-(4-chlorophenyl)-2-cyclopropyl-1-propanone (I).

The present invention further discloses a process for preparing a derivative of alkoxy propylene with the structure of formula (III), where α-alkoxy p-chlorobenzyl phosphonate with the structure of formula (II) and cyclopropyl methyl ketone are subjected to a Homer-Wadsworth-Emmons reaction in the presence of a base, so as to prepare the derivative of alkoxy propylene with the structure of formula (III);

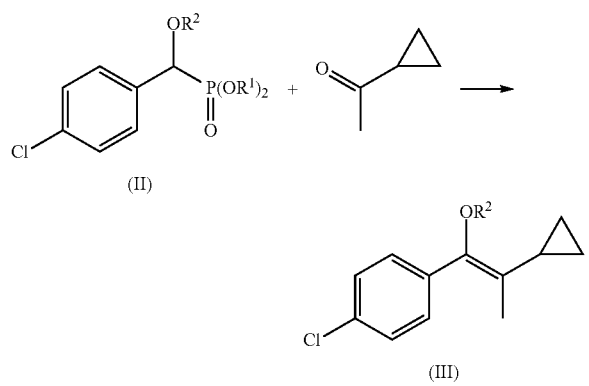

where, definitions of R$^1$ and R$^2$ as well as detailed process for preparation of the derivative (III) are the same as above.

The present invention has the following advantageous effects:

The present invention provides a novel process for preparing 1-(4-chlorophenyl)-2-cyclopropyl-1-propanone (I) by using α-alkoxy p-chlorobenzyl phosphonate (II) and cyclopropyl methyl ketone as the starting materials. Compared with the known methods recorded in the prior art, the process of the present invention features favorable convenience, safe operation and good economic feasibility, and is suitable for large-scale development.

EXAMPLES

Example 1

Preparation of 1-chloro-4-(2-cyclopropyl-1-methoxypropene-1-yl)benzene (III, R$^2$=methyl)

A mixture of diethyl α-methoxy p-chlorobenzyl diethyl phosphonate (30.7 g, 0.10 mol) [prepared by using 4-chlorobenzaldehyde dimethyl acetal and triethyl phosphite as raw materials with reference to a method described in Synthesis, (4), 330-332 (1984) or JOC, 56 (6), 2240-2244 (1991); EIMS (m/z): 294 (M+2), 292 (M)], and cyclopropyl methyl ketone (8.6 g, 0.10 mol) in dimethyl formamide (150 mL) was cooled to about 10° C. with an ice-water bath, and then potassium tert-butoxide (28.0 g, 0.25 mol) was slowly added in portions over a period of 5 h while maintaining the internal temperature not more than 30° C., and thereafter the resultant mixture was reacted at 20° C. to 25° C. for a further 2 h to finish the reaction.

The reaction solution was poured into 300 mL of water and extracted twice with each 100 mL of dichloromethane. The combined organic phase was washed with water, dried over anhydrous magnesium sulfate, and concentrated to yield 19.2 g of light yellow oil, i.e, a crude product of the title compound, with a purity of 92.1% identified by chromatographic analysis; This crude product was purified by silica gel column chromatography (n-hexane/dichloromethane) to obtain 14.8 g of colorless oily liquid with a purity of 99.3% identified by chromatographic analysis.

EIMS (m/z): 224 (M+2), 222 (M); $^1$H NMR: δ 0.12-0.40 (m, 4H), 0.90 (m, 1H), 1.72 (s, 3H), 3.50 (s, 3H), 7.18-7.22 (m, 4H).

Example 2

Preparation of 1-chloro-4-(2-cyclopropyl-1-ethoxypropene-1-yl)benzene (III, $R^2$=ethyl)

By reference to a method described in JOC, 56 (6), 2240-2244 (1991), a mixture of 4-chlorobenzaldehyde diethyl acetal (33.5 g, 0.15 mol), and trimethyl phosphate (21.1 g, 0.17 mol) in dichloromethane (250 mL) was cooled to less than −10° C. by ice-salt cooling, and then 50 g of zinc chloride was slowly added; The resultant mixture was allowed to warm to room temperature, and reacted over a period of 60 h while being fully stirred; Solid in the reaction mixture was separated off, and the filtered organic solution was washed with water (3×150 mL), dried over anhydrous magnesium sulfate, and concentrated to afford 34.2 g of dimethyl α-ethoxy p-chlorobenzyl phosphonate as light yellow oil with a purity of 94.8%, identified by chromatographic analysis. EIMS (m/z): 280 (M+2), 278 (M).

To a solution of dimethyl α-ethoxy p-chlorobenzyl phosphonate (29.4 g, 0.10 mol), obtained from the above reaction step, in dimethyl sulfoxide (100 mL), was added sodium amide (8.0 g, 0.20 mol) in portions, and the resulting mixture was stirred at room temperature for 0.5 h. Thereafter, cyclopropyl methyl ketone (10.2 g, 0.12 mol) was slowly added dropwise to the mixture while maintaining the internal temperature not more than 30° C. under ice-water cooling. The resulting reaction mixture was stirred at 20° C. to 25° C. over a period of 4 h to finish the reaction. The reaction solution was poured into 300 mL of water, and extracted twice, each with 100 m of toluene. The combined organic phase was washed with water, dried over anhydrous magnesium sulfate, and concentrated to obtain 21.0 g of light yellow oil, a crude product of the title compound, with a purity of 92.5% identified by chromatographic analysis. This crude product was purified by silica gel column chromatography (n-hexane/dichloromethane) to afford 16.5 g of colorless oily liquid, with a purity of 99.0%.

EIMS (m/z): 238 (M+2), 236 (M); $^1$H NMR: δ 0.10-0.40 (m, 4H), 0.91 (m, 1H), 1.22 (t, J=6.1 Hz, 3H) 1.71 (s, 3H), 3.98 (q, J=6.1 Hz, 2H), 7.18-7.22 (m, 4H).

Example 3

Preparation of 1-(4-chlorophenyl)-2-cyclopropyl-1-propanone (I)

A mixture of 1-chloro-4-(2-cyclopropyl-1-methoxypropene-1-yl)benzene (III, $R^2$=methyl) (11.2 g, 0.05 mol) obtained in Example 1, tetrahydrofuran 50 mL and 10% hydrochloric acid (50 mL), was stirred at room temperature for 3 h to finish the reaction. The reaction mixture was diluted with 50 mL of water, and extracted twice with each 50 mL of dichloromethane. The combined organic phase was washed with water, dried over anhydrous magnesium sulfate, and evaporated to afford 10.2 g of the title compound as oily liquid, with a purity of 98.6% identified by chromatographic analysis.

Embodiment 4

Preparation of 1-(4-chlorophenyl)-2-cyclopropyl-1-propanone (I)

A mixture of 1-chloro-4-(2-cyclopropyl-1-ethoxypropene-1-yl)benzene (III, $R^2$=ethyl) (12.0 g, 0.05 mol) obtained in Example 2, methanol (50 mL) and 15% hydrochloric acid (40 mL), was stirred at room temperature for 4 h to finish the reaction. The reaction mixture was diluted with 50 mL of water, and extracted twice with each 50 mL of toluene. The combined organic phase was washed with water, dried with anhydrous magnesium sulfate, and concentrated to give 10.4 g of the title compound as oily liquid, with a purity of 98.3%, identified by chromatographic analysis.

Example 5

Preparation of 1-(4-chlorophenyl)-2-cyclopropyl-1-propanone (I)

A mixture of diethyl α-methoxy p-chlorobenzyl phosphonate (37.0 g, 0.12 mol), and cyclopropyl methyl ketone (8.6 g, 0.10 mol) in tert-butyl alcohol (60 mL), was cooled to about 10° C. with an ice-water bath. To the mixture was slowly added dropwise a solution of potassium tert-butoxide (27.0 g, 0.24 mol) in tert-butanol (90 mL) while maintaining the internal temperature not more than 30° C. The resulting mixture was stirred at 20° C. to 25° C. over a period of 3 h to finish the reaction. Thus, the reaction solution was poured into 300 mL of water, and extracted twice with each 100 mL of toluene. The combined organic phase was washed with water and concentrated to give a crude product of 1-chloro-4-(2-cyclopropyl-1-methoxypropene-1-yl)benzene (III, $R^2$=methyl) as light yellow oil, 18.2 g with a purity of 91.8% identified by chromatographic analysis. This was directly used for the hydrolysis of the next step.

The crude product of 1-chloro-4-(2-cyclopropyl-1-methoxypropene-1-yl)benzene (III, $R^2$=methyl) obtained in the above step was mixed with 10% hydrochloric acid (150 mL), and the resultant mixture was stirred at room temperature for 8 h, and then extracted twice with each 80 mL of dichloromethane. The combined organic phase was washed with water, dried over anhydrous magnesium sulfate, and evaporated to give 15.6 g of the title compound as orange oily liquid, with a purity of 92.8% identified by chromatographic analysis.

Embodiment 6

Preparation of 1-(4-chlorophenyl)-2-cyclopropyl-1-propanone (I)

A mixture of diethyl α-methoxy p-chlorobenzyl phosphonate (61.5 g, 0.20 mol), cyclopropyl methyl ketone (20.5 g, 0.24 mol), dimethyl formamide (25 mL) and toluene (250 mL) was cooled to about 10° C. with an ice-water bath. To the mixture was slowly added sodium amide (16.0 g, 0.40 mol) in portions over period of 4 h while maintaining the internal temperature not more than 30° C. The resulting mixture was stirred at 20° C. to 25° C. for a further 3 h; To the mixture was added 200 mL of water, and stirred for 0.5 h. Thus the resultant mixture was allowed to form two layers, the separated aqueous phase was extracted with additional 100 mL of toluene. The combined organic phase was the toluene solution of 1-chloro-4-(2-cyclopropyl-1-methoxypropene-1-yl)benzene (III, $R^2$=methyl). This was directly used for the hydrolysis of the next step.

The toluene solution of 1-chloro-4-(2-cyclopropyl-1-methoxypropene-1-yl)benzene (III, $R^2$=methyl) obtained in the above step was mixed with 10% hydrochloric acid (250 mL), and the resulting mixture was stirred at room temperature for 10 h, and then allowed to form two layers. The separated organic phase was washed with an aqueous solution of 5% sodium bicarbonate, and then washed with water to neutral pH, and concentrated to obtain 36.0 g of orange oily liquid, a crude product of the title compound, with a purity of 93.1%. This crude product was distilled under reduced pressure to afford 30.2 g of 1-(4-chlorophenyl)-2-cyclopropyl-1-propanone (I) as light yellow oil, with a purity of 97.6%, identified by chromatographic analysis.

What is claimed is:

1. A compound of formula (III),

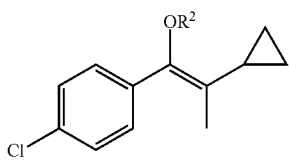
(III)

wherein, R² is a C1-C4 alkyl.

2. The compound according to claim 1, where R² in Formula (III) is methyl or ethyl.

3. A process for producing the compound of claim 1 comprising reacting an α-alkoxy p-chlorobenzyl phosphonate of Formula (II) with cyclopropyl methyl ketone in the presence of a base to produce the compound of Formula (III):

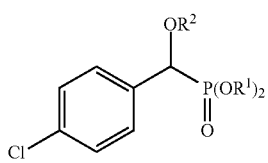
(II)

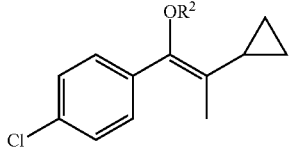
(III)

wherein R¹ is methyl or ethyl; and R² in Formula (II) is identical with those in Formula (III).

4. The process according to claim 3, wherein said base is sodium amide, sodium tert-butoxide or potassium tert-butoxide.

5. The process according to claim 3, wherein the reaction temperature is between 0° C. to 40° C.

6. The process according to claim 3, wherein the compound of Formula (III) is further reacted as an intermediate to produce 1-(4-chlorophenyl)-2-cyclopropyl-1-propanone.

7. The compound according to claim 1, which has been obtained by a process comprising reacting an α-alkoxy p-chlorobenzyl phosphonate of Formula (II) with cyclopropyl methyl ketone in the presence of a base to produce the compound of Formula (III):

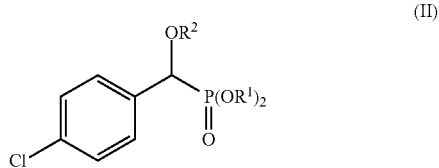
(II)

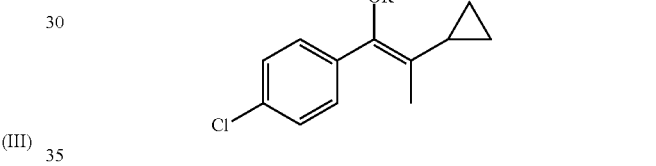
(III)

wherein R¹ is methyl or ethyl; and R² in Formula (II) is identical with those in Formula (III).

8. The compound according to claim 7, wherein R² is methyl or ethyl.

* * * * *